US00PP28669P2

(12) United States Plant Patent
Yanny

(10) Patent No.: US PP28,669 P2
(45) Date of Patent: Nov. 21, 2017

(54) ***RHUS* PLANT NAMED 'FINE TEXTURED COMPACT SELECT A'**

(50) Latin Name: *Rhus aromatica*
Varietal Denomination: Fine Textured Compact Select A

(71) Applicant: JN Plant Selections, LLC, Milwaukee, WI (US)

(72) Inventor: Michael D. Yanny, Milwaukee, WI (US)

(73) Assignee: JN PLANT SELECTIONS, LLC, Milwaukee, WI (US)

( * ) Notice: Subject to any disclaimer, the term of this patent is extended or adjusted under 35 U.S.C. 154(b) by 0 days.

(21) Appl. No.: 14/999,979

(22) Filed: Jul. 21, 2016

(51) Int. Cl.
*A01H 5/00* (2006.01)

(52) U.S. Cl.
USPC ..... Plt./226

(58) Field of Classification Search
USPC ..... Plt./226
CPC ..... A01H 5/00
See application file for complete search history.

*Primary Examiner* — Kent L Bell
(74) *Attorney, Agent, or Firm* — Penny J Aguirre

(57) ABSTRACT

A new cultivar of *Rhus* named, 'Fine Textured Compact Select A', that is characterized by its compact, dense, and freely branching plant habit without shearing, its small leaves that give it a fine textured appearance, its red fall foliage color, its resistance to leaf mites, and its cuttings that are readily rooted.

2 Drawing Sheets

Botanical classification: *Rhus aromatica.*
Cultivar designation: 'Fine Textured Compact Select A'.

BACKGROUND OF THE INVENTION

The present invention relates to a new and distinct cultivar of *Rhus aromatica*, and will be referred to hereafter by its cultivar name, 'Fine Textured Compact Select A'. 'Fine Textured Compact Select A' is grown for use as a landscape shrub, groundcover, or hedge.

'Fine Textured Compact Select A' was discovered by the Inventor in 2011 as a chance seedling growing in a container production block at his nursery in Menomonee Falls, Wis. The containers had been planted with seedlings derived from the open pollination of seedlings of *Rhus aromatica*. The characteristics of the parent plants is unknown.

Asexual propagation of the new cultivar was first accomplished by softwood stem cuttings under the direction of the Inventor in July of 2013 in Menomonee Falls, Wis. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar, which in combination distinguish 'Fine Textured Compact Select A' as a new and distinct cultivar of *Rhus*.

1. 'Fine Textured Compact Select A' exhibits a compact, dense, and freely branching plant habit without shearing.
2. 'Fine Textured Compact Select A' exhibits small leaves that give it a fine textured appearance.
3. 'Fine Textured Compact Select A' exhibits red fall foliage color.

4. 'Fine Textured Compact Select A' exhibits resistance to leaf mites (*Aculops rhois*).
5. 'Fine Textured Compact Select A' exhibits cuttings that are readily rooted.

Typical plants of *Rhus aromatica* differ from 'Fine Textured Compact Select A' in being less freely branched and in having leaves that are larger in size. 'Fine Textured Compact Select A' can also be compared to the *Rhus aromatica* cultivar 'Gro-low' (not patented) and 'JN Free Branch Select B' (not patented). 'Gro-low' is similar to 'Fine Textured Compact Select A' in having a low growing plant habit. 'Gro-low' differs from 'Fine Textured Compact Select A' in having a wider and lower growing plant habit, in being less freely branched, in having leaves that are larger in size (less fine textured), in being more difficult to root, and in being more susceptible to leaf mites. 'JN Free Branch Select B' is similar to 'Fine Textured Compact Select A' in being well-branched but differs from 'JN Free Branch Select B' in having foliage that is less fine textured and in not having a compact plant habit.

BRIEF DESCRIPTION OF THE DRAWINGS

The accompanying colored photographs illustrate the overall appearance and distinct characteristics of the new *Rhus*. The photographs in FIG. 1, FIG. 2 and FIG. 3 were taken of a plant eight years in age as grown outdoors in a trial garden in Menomonee Falls, Wis.

The photograph in FIG. 1 provides a side view of a plant of 'Fine Textured Compact Select A' in summer.

Figure 1:
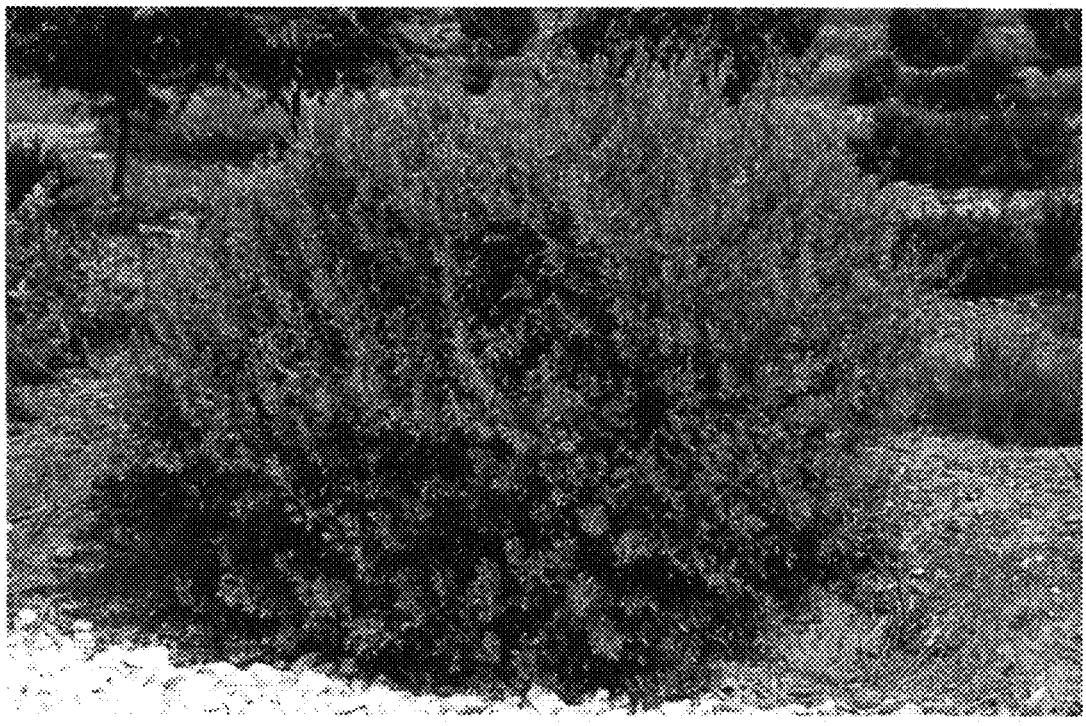
Figure 2:
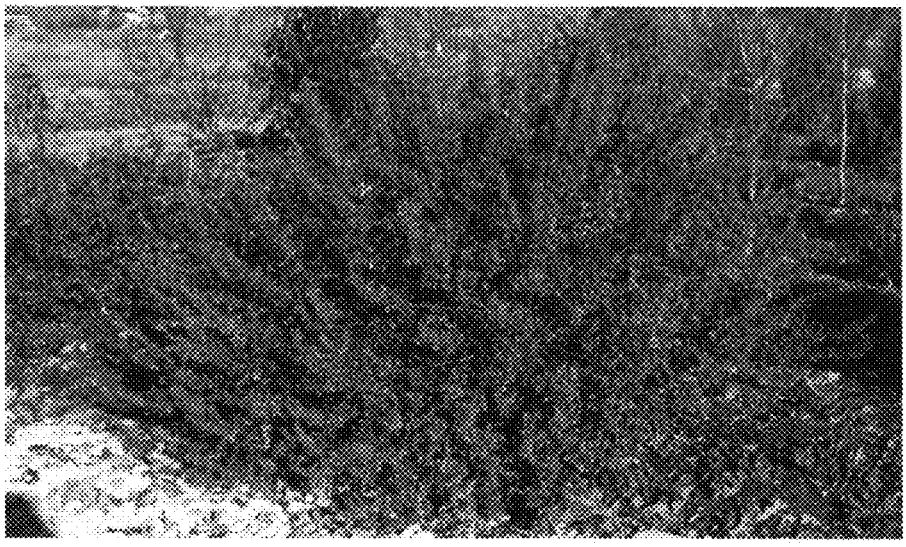

The photograph in FIG. 2 provides a side view of a plant of 'Fine Textured Compact Select A' in fall.

Figure 3:
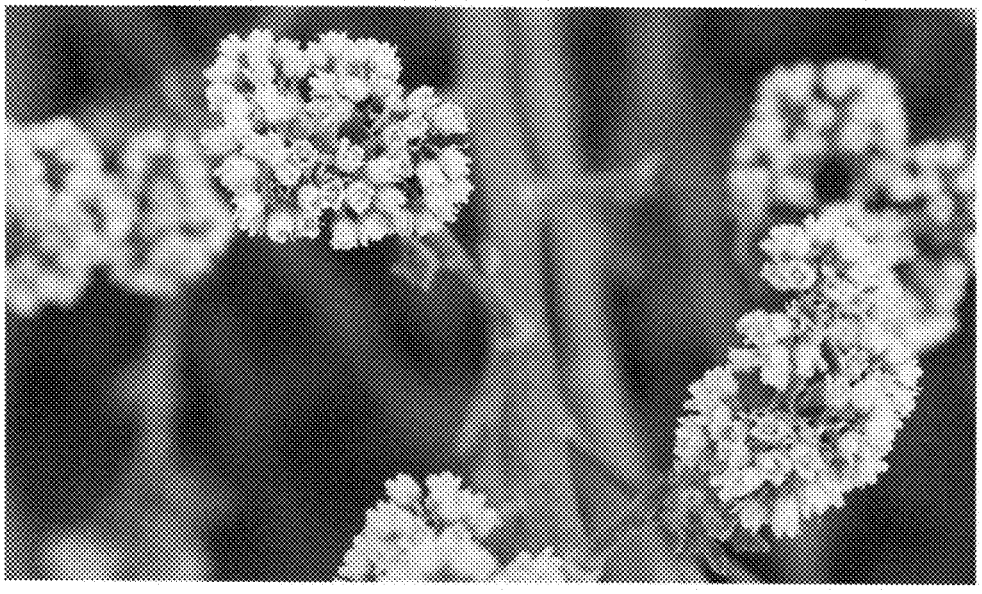
Figure 4:
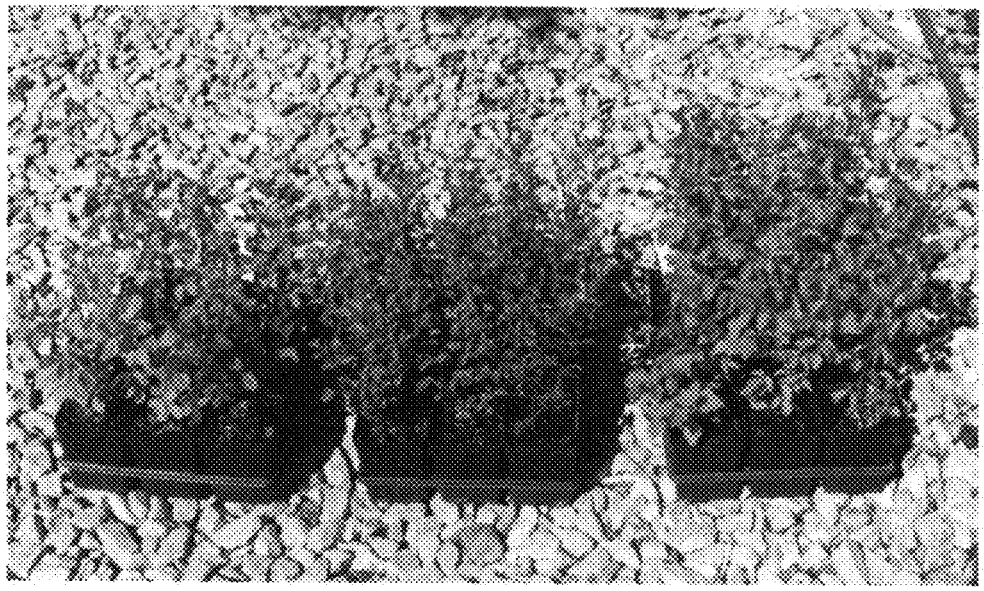

The photograph in FIG. 3 provides a close-up view of the inflorescences of 'Fine Textured Compact Select A'. The photograph in FIG. 4 was taken of plants one year in age as grown outdoors in 1-qt pots in Menomonee Falls, Wis. and provides a comparison between 'Gro-low' (left), 'Fine Textured Compact Select A' (center) and 'JN Free Branch Select B' (right, not patented).

The colors in the photographs are as close as possible with the photographic and printing technology utilized and the color values cited in the detailed botanical description accurately describe the colors of the new *Rhus*.

DETAILED BOTANICAL DESCRIPTION OF THE PLANT

The following is a detailed description of four year-old plants of the new cultivar as grown outdoors in a 3-gallon container in Menomonee Falls, Wis. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Mid-May in southern Wisconsin.

*Plant type*.—Perennial deciduous shrub.

*Plant habit*.—Compact and densely and freely branched.

*Height and spread*.—An 8 year-old plant in the landscape will reach an average of 1.2 m in height and 2.1 m in width.

*Hardiness*.—At least in U.S.D.A. Zones 4 to 9.

*Diseases and pests*.—Resistance to leaf mites (*Aculops rhois*) has been observed.

*Root description*.—Woody with fibrous secondary roots, woody N199A in color, fibrous N199D in color

*Propagation*.—Softwood stem cuttings.

*Time required for root development*.—An average of three weeks for root initiation and an average of 1 year to produce a young plant in a 1-qt container.

*Growth rate*.—Moderate.

Branch description:

*Branch size*.—Main Trunk; 4 cm in length and 2 cm in diameter, lateral branches; average of 50 cm in length and 7 mm in diameter, tertiary branches; up to 26 cm in length and 3.5 m in diameter.

*Branch shape*.—Rounded.

*Branch color*.—Young shoots; 197B, mature branches and trunk; N199B.

*Branch surface*.—Young shoots; glabrous, branches; mature stems; relatively smooth with numerous horizontal lenticels; N119B in color, 1.5 mm in length, 0.5 mm in width, average of 40 per branch 2 cm in length, trunk; fissured bark.

*Branch strength*.—Strong.

*Internode length*.—Branch internodes; an average of 2 cm for tertiary branches, leaf internodes an average of 9 mm.

*Branching habit*.—Well-branched, an average of 4 lateral branches, 10 secondary branches per lateral branch and an average of 3 tertiary branches per secondary branch.

*Branching aspect*.—Lateral branches typical angles of 0° to 30° (vertical=0°).

*Branch buds*.—Imbricate, N199A in color with margins 155A, average of 6 mm in length and 4 mm in width.

Foliage description:

*Leaf shape*.—Trifoliate, overall ovate.

*Leaf division*.—Trifoliate.

*Leaf attachment*.—Petiolate.

*Leaf size*.—Average of 3.7 cm in length and 4 cm in width.

*Leaf arrangement*.—Alternate.

*Leaflet base*.—Attenuate.

*Leaflet apex*.—Acute.

*Leaflet venation*.—Pinnate, color 144D on upper and lower surface.

*Leaflet margins*.—Crenate.

*Leaf arrangement*.—Alternate.

*Leaflet surface*.—Glabrous and dull on both surfaces.

*Leaflet color*.—Upper surface young foliage; 138A, lower surface young foliage; 138B, mature foliage upper surface; 137A, mature lower surface foliage; 138A, color changes to 42A in the fall.

*Leaflet number*.—An average of 14 per tertiary branch.

*Leaflet size*.—An average of 2.5 cm in length and 1.5 cm in width (lateral leaflets slightly smaller).

*Leaf aspect*.—Held upward at about a 45° angle to stem.

*Petioles*.—An average of 1.6 cm in length and 1 mm in diameter, 144C in color.

Flower description:

*Inflorescence type*.—Panicle of dense clusters arranged in whorls on terminals and axillary nodes.

*Inflorescence size*.—Up to 5 cm in height and 2 cm in width with individual clusters an average of 9 mm in length and width.

*Inflorescence quantity*.—An average of 20 per lateral branch, an average of 9 individual clusters per panicle.

*Inflorescence lastingness*.—About 1 week.

*Flower type*.—Urceolate.

*Flower fragrance*.—Not detected.

*Flower bud description*.—Ovate in shape, an average of 2 mm in length and diameter (at base), color N144D with sepal portion 144A.

*Bracts*.—Individual clusters emerge from imbricate bracts held in a conical shaped structure a average of 4 mm in length and 2 mm in width, each bract is ovate in shape, an average of 1 mm in length and width, 175A in color, surface texture is smooth with highly pubescent margins.

*Flower quantity*.—Up to 80 per inflorescence and 10 per individual cluster.

*Flower size*.—An average of 2.5 mm in depth and diameter.

*Flower aspect*.—Outwards in all directions.

*Peduncle*.—Main peduncles (rachis of panicle); up to 4.5 cm in length and an average of 1.5 mm in width, 165A in color, surface texture is finely pubescent, internodes of clusters an average of 3 mm, on clusters; stout, an average of 3 mm in length and 2 mm in diameter, 176A in color and densely covered with pubescence 156A in color, primary peduncle held at an average angle of 45° main peduncle.

*Pedicels*.—An average of 2 mm in length and 0.5 mm in diameter, 144B in color, held upright, moderate strength, glabrous surface texture.

*Petal description.*—5, ovate in shape, fused at base, entire margins, acute apex, smooth surface texture, an average of 2 mm in length and 1 mm in width, color; when opening both surfaces; 145D, color when mature both surfaces; 4D.

*Sepal description.*—5, broadly lanceolate in shape, held on petal surface, entire margin, acuminate apex, fused base, shiny and glandular on both surfaces, an average of 1.5 mm in length and 0.5 mm in width, color; upper and lower surfaces; 144A.

Reproductive organs:

*Gynoecium.*—1 pistil, stigma; 3-parted club-shaped, 7 mm in diameter and 4D in color, style; an average of 1.5 mm in length and 71A in color, ovary is 145A in color.

*Androecium*.—None observed, female selection.

*Fruit*.—Held in clusters on the pedicle, up to 5 berries per pedicel, round to oblong shape with very minute protruding rounded apex that contains 3 small raised dots, an average of 8 mm in diameter, young fruit color inner and outer surface; 144A, mature fruit color outer surface; N45A, apex slightly visible about 36A with 3 tiny dots of 203A, mature fruit color inner surface; a blend of 31A and N45A, outer surface is shiny and densely covered with long hairs up to 2 mm in length and NN155A in color, inside surface is glabrous and shell-like, surrounding the seed with no flesh.

*Seed.*—Obicular in shape and flattened with a mucronate apex and base, color; striations of 165A, 169A and 170B, surface is slightly glossy and covered in striations, an average of 6 mm in length and width.

It is claimed:

1. A new and distinct cultivar of *Rhus* plant named 'Fine Textured Compact Select A' as herein illustrated and described.

* * * * *